United States Patent [19]

Gehret et al.

[11] Patent Number: 4,824,845
[45] Date of Patent: Apr. 25, 1989

[54] PESTICIDAL COMPOSITIONS

[75] Inventors: Jean-Claude Gehret, Aesch; Odd Kristiansen, Möhlin, both of Switzerland

[73] Assignee: Ciba-Geigy Corporation, Ardsley, N.Y.

[21] Appl. No.: 233,870

[22] Filed: Aug. 17, 1988

Related U.S. Application Data

[63] Continuation of Ser. No. 810,482, Dec. 18, 1985, abandoned, Continuation of Ser. No. 676,904, Nov. 30, 1984, abandoned.

[30] Foreign Application Priority Data

Dec. 2, 1983 [CH] Switzerland ..................... 6466/83
Nov. 2, 1984 [CH] Switzerland ..................... 5267/84

[51] Int. Cl.$^4$ .................... A01N 43/68; C07D 251/70
[52] U.S. Cl. .................................. 514/245; 544/197; 544/196
[58] Field of Search .................. 544/197; 514/245

[56] References Cited

U.S. PATENT DOCUMENTS

| | | | |
|---|---|---|---|
| 3,218,148 | 11/1965 | Knusli | 544/196 |
| 3,236,846 | 2/1966 | Knüsli et al. | 260/249.8 |
| 3,419,535 | 12/1968 | Schlumbom et al. | 544/196 |
| 4,160,832 | 7/1979 | Laanio et al. | 544/197 |

FOREIGN PATENT DOCUMENTS

| | | |
|---|---|---|
| 685713 | 5/1964 | Canada . |
| 394703 | 12/1965 | Switzerland . |
| 527834 | 10/1940 | United Kingdom . |
| 922830 | 4/1963 | United Kingdom . |

Primary Examiner—John M. Ford
Attorney, Agent, or Firm—Kevin T. Mansfield; Edward McC. Roberts

[57] ABSTRACT

Novel substituted acylamino-s-triazine compounds of the formula

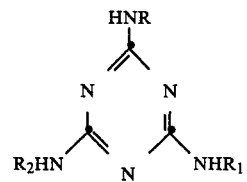

wherein R is $C_1$-$C_4$-alkyl, $R_1$ is hydrogen, or $C_2$—$C_{12}$-acyl which is unsubstituted or substituted by halogen or $C_1$—$C_4$-alkoxy, and $R_2$ is $C_2$—$C_{12}$-acyl which is unsubstituted or substituted by halogen or $C_1$—$C_4$-alkoxy, including the salts thereof. The novel compounds have valuable insecticidal and laryicidal properties, and can be used as active substances for controlling phytoparasitic and zooparasitic insects, expecially the larvae thereof, amongst these in particular ectoparasites.

10 Claims, No Drawings

PESTICIDAL COMPOSITIONS

This application is a continuation of application Ser. No. 810,482, filed Dec. 18, 1985, now abandoned, which in turn is a continuation of application Ser. No. 676,904, filed Nov. 30, 1984, now abandoned.

The present invention relates to novel substituted acylamino-s-triazine compounds and salts thereof, to processes for producing them, and to their use for controlling harmful insects and ectoparasites.

The novel compounds have the general formula I

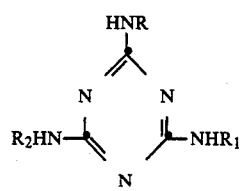

wherein R is $C_1$–$C_4$-alkyl, including cycloalkyl, $R_1$ is hydrogen, or $C_2$–$C_{12}$-acyl which is unsubstituted or substituted by halogen or $C_1$–$C_4$-alkoxy, and $R_2$ is $C_2$–$C_{12}$-acyl which is unsubstituted or substituted by halogen or $C_1$–$C_4$-alkoxy, and include the salts thereof.

Alkyl groups R by themselves and as moiety of acyl groups denoted by $R_1$ and $R_2$ are straight-chain, branched-chain or cyclic alkyl groups. Examples thereof are: methyl, ethyl, the isomers of propyl, butyl, pentyl, hexyl, heptyl, octyl, nonyl, decyl and undecyl, as well as cyclopropyl, cyclobutyl, cyclopentyl and cyclohexyl.

Identical or different halogen substituents of the acyl groups denoted by $R_1$ and $R_2$ are fluorine, chlorine, bromine or iodine.

Alkoxy groups as acyl substituents are methoxy or ethoxy, or the isomers of propoxy and butoxy.

Compounds of the formula I which are preferred by virtue of their particularly advantageous action are those
wherein
$R_1$ is hydrogen, or $C_2$–$C_{12}$-acyl which is unsubstituted or substituted by halogen,
$R_2$ is $C_2$–$C_{12}$-acyl which is unsubstituted or substituted by halogen, and
R has the meanings defined under the formula I; or wherein
$R_1$ is hydrogen, or $C_2$–$C_{12}$-acyl which is unsubstituted or substituted by $C_1$–$C_4$-alkoxy,
$R_2$ is $C_2$–$C_{12}$-acyl which is unsubstituted or substituted by $C_1$–$C_4$-alkoxy, and
R has the meanings defined under the formula I; or wherein
R is cyclopropyl or iso-propyl,
$R_1$ is hydrogen, or $C_2$–$C_{12}$-acyl which is unsubstituted or substituted by chlorine, and
$R_2$ is $C_2$–$C_{12}$-acyl which is unsubstituted or substituted by chlorine; or
wherein
R is cyclopropyl or iso-propyl,
$R_1$ is hydrogen, or $C_2$–$C_{12}$-acyl which is unsubstituted or substituted by methoxy or ethoxy, and
$R_2$ is $C_2$–$C_{12}$-acyl which is unsubstituted or substituted by methoxy or ethoxy; or
wherein
R is cyclopropyl or iso-propyl,
$R_1$ is hydrogen, and
$R_2$ is $C_2$–$C_{12}$-acyl which is unsubstituted or substituted by chlorine; or especially those compounds of the formula I
wherein
R is cyclopropyl,
$R_1$ is hydrogen, and
$R_2$ is $C_2$–$C_{12}$-acyl.

The following individual compounds are preferred: 2-cyclopropylamino-4-acetylamino-6-amino-1,3,5-triazine, 2-cyclopropylamino-4-methoxyacetylamino-6-amino-1,3,5-triazine, 2-cyclopropylamino-4-propanoylamino-6-amino-1,3,5-triazine, 2-cyclopropylamino-4-butanoylamino-6-amino-1,3,5-triazine, and 2-cyclopropylamino-4-(2-methylpropanoylamino)-6-amino-1,3,5-triazine.

By the term 'salts of acylamino-s-triazine compounds of the formula I' are meant addition salts of inorganic and organic acids. Examples of inorganic acids are: hydrochloric acid, hydrobromic acid, hydriodic acid, sulfuric acid, phosphoric acid, phosphorous acid and nitric acid. Examples of organic acids are: trifluoroacetic acid, trichloroacetic acid, formic acid, oxalic acid, succinic acid, maleic acid, lactic acid, glycolic acid, aconitic acid, citric acid, benzoic acid, benzenesulfonic acid and methanesulfonic acid.

The compounds of the formula I are produced by reacting compounds of the formula II

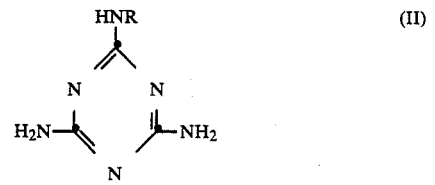

with compounds of the formula IIIa

or of the formula IIIa'

to give compounds of the formula Ia

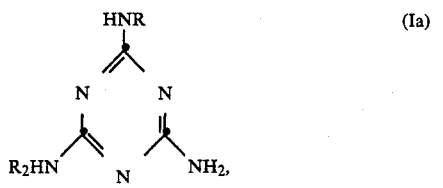

and optionally reacting compounds of the formula Ia with compounds of the formula IIIb

or of the formula IIIb'

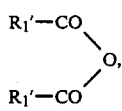

to obtain compounds of the formula Ib

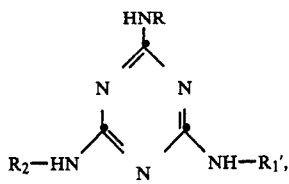

in which $R_1'$ and $R_2$ independently of one another are each $C_2$-$C_{12}$-acyl which is unsubstituted or substituted by halogen or $C_1$-$C_4$-alkoxy, and Hal is halogen, preferably chlorine, and R has the meanings defined under the formula I.

The process described in the foregoing is performed under normal pressure in inert solvents or diluents, in the presence of a base, at temperatures of 0° to 120° C., preferably of 40° to 80° C. Suitable solvents or diluents are for example: alkanes, such as n-pentane, as well as homologues thereof, including the isomers up to n-heptadecane; ethers, such as diethyl ether, dipropyl ether, dibutyl ether, dimethoxyethane, dioxane or tetrahydrofuran; chlorinated hydrocarbons, such as chloroform, methylene chloride, carbon tetrachloride or chlorobenzene; or aromatic hydrocarbons, such as benzene, toluene or the xylenes. There can also be used in the process other inert solvents or diluents. And suitable bases are for example alkylamines, such as triethylamine, or diisopropylethylamine, and also pyridine or n-methylpyrrolidone.

The process described in the foregoing for producing compounds of the formula I is known in general from the literature (cf. The Chemistry of Heterocyclic Compounds, Vol. 13: s-Triazines and Derivatives, Interscience Publishers Inc., New York, 1959).

The starting materials of the formulae II, IIIa, IIIa', IIIb and IIIb' are known and can be produced by correspondingly known processes.

Diamino and triamino derivatives of s-triazines are known from the U.S. Pat. No. 3,189,521 as being chemosterilants for adult house flies (*Musca domestica*).

The chemosterilising action on insects of 2,4,6-triamino-s-triazine derivatives (melamine derivatives) is described also by S. Nagasawa et al., Botyu-Kagaku 39 (4), 105 (1974). A. B. Borkovec and A. B DeMilo (J. Med. Chem. 10 (5), 457 (1967) and also G. C. LaBrecque, R. L. Fye, A. B. DeMilo and A. B. Borkovec (J. Econ. Entomol. 61 (6), 1621 (1968) describe moreover the chemosterilising action of, inter alia, 2-cyclohexylamino-4,6-diamino-s-triazine, 2-cyclohexylamino-4,6-dihexylamino-s-triazine and 2,4,6-triscyclohexylamino-s-triazine and salts thereof on adult house flies (*Musca domestica*). Furthermore, the insecticidal action of cyclopropylamino-triazine derivatives is known from the U.S. Pat. No. 4,225,598.

It has now been established that the compounds of the formula I surprisingly have a pronounced larvicidal action against the larvae of insects, particularly Diptera larvae. In contrast to the insecticidal chemosterilants mentioned above, the compounds of the formula I act above all on the juvenile stages of the insects. The action results in the dying of the egg larvae or in the prevention of the hatching of adults from the pupae. The action of the compounds of the formula I is not to be compared with the mode of action of conventional insecticides, chemosterilants or juvenile-hormone analogues.

The active substances of the formula I are used for controlling animal ectoparasites and hygiene pests, particularly of the order Diptera, and of the families: Culicidae, Simuliidae, Tipulidae, Muscidae and Calliphoridae. The compounds of the formula I prove to be especially effective against larvae of the blowfly (*Lucilia sericata* and *Lucilia cuprina*) belonging to the Calliphoridae family, and also against fly larvae and mosquito larvae.

In addition, the compounds of the formula I are effective against members of the orders Siphonaptera (for example blood-sucking fleas).

Besides their action against mosquitoes and flies, for example *Aedes aegypti* and *Musca domestica*, compounds of the formula I also have a favourable action for use in controlling insects that damage plants by eating, in crops of ornamental plants and productive plants, in particular in rice crops (for example against *Nilaparvata lugens* and *Laodelphax striatellus*).

In their activity, the compounds according to the invention exhibit a spectrum which, extending beyond the larval stage, embraces also the remaining stages of development of the parasites, as well as the oviposition of fertile eggs.

The compounds of the formula I are distinguished also, in a completely surprising manner, by their biological long-term effect, which constitutes a special feature of these compounds. This prolonged mode of action can, depending on the method of application, extend over a period of more than three months, which, compared with the mode of action of known preparations, offers many advantages.

In the application of the active substances according to the invention for livestock-housing hygiene, there is rendered possible for example an extremely low frequency of application, so that in moderate climatic regions with a three-month summer season, a single application is sufficient to effectively reduce, in livestock housing, a development of the harmful Diptera larvae, which is normally promoted by the climatic conditions.

With the treatment of grazing animals with the compounds according to the invention, for example by means of cattle dips, pour-on methods or spray races, there is obtained by virtue of the surprising adhesive action of the active substances a long-lasting toxic effect against ectoparasites, such as harmful Diptera, on the skin and external parts of the animals. A premature washing off or washing out of the active substances, which have been applied to the surface of the productive animals, by the running-off of rain water can thus be prevented.

The particular advantage of the sustained action of the compounds of the formula I is felt especially in the case of the oral administration to useful animals. In this application process, the active substances exhibit in particular in the faeces excreted from the digestive tract an effective and prolonged insecticidal activity. Consequently, an infestation by harmful insects, especially Diptera, can be prevented before the occurrence of the pests in the vicinity of the animals, such as in cattle housing or in enclosures and on pasture land, because the Diptera larvae hatching from the deposited eggs are killed immediately. A particularly important factor with respect to this special form of application is that, by virtue of their structural properties, the compounds of the formula I behave physiologically indifferent to warm-blooded animals. This method of the specific control of the proliferation of the insects is considerably more efficient and at the same time more economical than the customary methods involving the large-area disinfection of livestock housing and enclosures.

For the control of pests, the compounds of the formula I according to the invention are used either alone or in the form of compositions, which additionally contain suitable carriers and/or additives, or mixtures of such substances. Suitable carriers and formulation auxiliaries can be solid or liquid and they correspond to the substances customarily used in formulation practice, for example natural or regenerated substances, solvents, dispersing agents, wetting agents, adhesives, thickeners or binders.

For application, the compounds of the formula I are processed, by the usual formulation procedures which are a part of common knowledge in the field of application techniques, into the form of dusts, emulsion concentrates, granulates, dispersions, sprays or solutions.

The compositions according to the invention are produced, in a manner known per se, by the intimate mixing and/or grinding of active ingredients of the formula I with the appropriate carriers, optionally with the addition of dispersing agents and solvents inert to the active ingredients. The active ingredients can be made up and used in the following forms:

solid preparations:
dusts, scattering agents and granulates (coated granulates, inpregnated granulates and homogeneous granulates);
liquid preparations:
(a) water-dispersible concentrates of active ingredient: wettable powders, pastes and emulsions;
(b) solutions: pour-on solutions and sprays.

The content of active ingredient in the preparations described in the foregoing is between 0.1 and 95% by weight, preferably between 1 and 80% by weight.

As active ingredients of compositions, the compounds of the formula I according to the invention are suitable, because of the diversity of the preparations available, for the control, in a multitude of ways, of parasites on or in the vicinity of animals, for example in livestock housing. They can thus be applied for example in cattle dips, spray races, pour-on solutions or hand sprays. The compounds can be used with great success also for the treatment of animal faeces by means of the feed-through method, and for the hygienic treatment of manure in livestock housing.

Example 1: Production of 2-cyclopropylamino-4-heptanoylamino-1,3,5-triazine

To a suspension of 33.2 g of 2,4-diamino-6-cyclopropylamino-1,3,5-triazine and 30.3 g of triethylamine in 800 ml of tetrahydrofuran are slowly added dropwise, at 60° C., 50.9 g of oenanthic acid anhydride dissolved in 100 ml of tetrahydrofuran. The reaction mixture is subsequently stirred overnight at 60° C.; active charcoal is then added and the mixture is filtered hot. The filtrate is concentrated by evaporation, and isopropanol is added. The product is obtained, after filtration and drying, in the form of a white crystalline powder having a melting point of 195°-197° C.

Example 2: Production of 2,4-bis-acetylamino-6-cyclopropylamino-1,3,5-triazine To a suspension of 12.45 g of 2,4-diamino-6-cyclopropylamino-1,3,5-triazine in 100 ml of pyridine are slowly added dropwise 12 g of acetyl chloride. The reaction mixture is subsequently stirred for 1 hour at 55° C. and then for 16 hours at room temperature. After filtration, washing of the filter residue with water and drying, the product is obtained in the form of white crystalline powder having a melting point of 267°-269° C.

Example 3: Production of 2-cyclopropylamino-4-acetylamino-6-amino-1,3,5-triazine To a suspension of 49.8 g of 2,4-diamino-6-cyclopropylamino-1,3,5-triazine and 45.5 g of triethylamine in 1200 ml of tetrahydrofuran are slowly added dropwise, at about 60° C. (in about 6 hours), 31.7 g of acetic acid anhydride dissolved in 100 ml of tetrahydrofuran. The reaction mixture is subsequently refluxed for 18 hours, filtered hot and then concentrated by evaporation until crystallisation commences. After the addition of about 300 ml of diethyl ether, the product if filtered off as white crystalline powder. It has a melting point of 190°-195° C.

Example 4: Production of 2-cyclopropylamino-4-propanoylamino-6-amino-1,3,5-triazine-HCl 2.2 g of 2-cyclopropylamino-4-propanoylamino-6-amino-1,3,5-triazine are dissolved in 6 ml of 2N HCl, and the solution is stirred for 5 minutes at room temperature. After concentration by evaporation and subsequent drying, the product is obtained in the form of white crystalline powder having a melting point of 210°-212° C.

Example 5: Production of 2-methoxyacetylamino-4-cyclopropylamino-6-amino-1,3,5-triazine To a suspension of 8.3 g of 2,4-diamino-6-cyclopropylamino-1,3,5-triazine and 7.1 g of triethylamine in 250 ml of tetrahydrofuran are slowly added dropwise, at about 60° C. (in about 5 hours), 8.9 g of methoxyacetic acid anhydride dissolved in 30 ml of tetrahydrofuran. The reaction mixture is subsequently refluxed for 18 hours; it is filtered hot and then concentrated by evaporation until the commencement of crystallisation. After the addition of about 300 ml of diethyl ether, the product is filtered off in the form of white crystalline powder having a melting point of 152°-157° C.

Example 6: Production of 2,4-bis-methoxyacetylamino-6-cyclopropylamino-1,3,5-triazine 7.2 g of methoxyacetyl chloride are slowly added dropwise to a suspension of 5.0 g of 2,4-diamino-6-cyclopropylamino-1,3,5-triazine in 50 ml of pyridine. The reaction mixture is subsequently stirred for 1 hour at 55° C. and then for 16 hours at room temperature. After filtration of the reaction mixture, washing of the filter residue with water and finally drying, the product is obtained as white crystalline powder having a melting point of 175°-180° C.

The following compounds are produced in a manner analogous to that described in the above Examples.

TABLE 1

[Structure: cyclopropyl-C(=NH)-N=C(NH₂)-N=C(NHR₁)- triazine-like system]

| No. | R₁ | Salt | m.p. [°C.] |
|---|---|---|---|
| 1 | —CO—CH$_3$ | — | 190–195 |
| 2 | —CO—CH$_3$ | HCl | 245–247 |
| 3 | —CO—C$_2$H$_5$ | — | 226–229 |
| 4 | —CO—C$_2$H$_5$ | HCl | 210–212 |
| 5 | —CO—C$_3$H$_7$(n) | — | 216–218 |
| 6 | —CO—C$_3$H$_7$(n) | HCl | 95–100 (amorph) |
| 7 | —CO—C$_3$H$_7$(i) | — | 232–236 |
| 8 | —CO—C$_3$H$_7$(i) | HCl | 155–160 |
| 9 | —CO—C$_4$H$_9$(t) | — | 80–85 (amorph) |
| 10 | —CO—C$_4$H$_9$(t) | HCl | 60–65 (amorph) |
| 11 | —CO—C$_4$H$_9$(n) | — | 182–183 |
| 12 | —CO—C$_4$H$_9$(n) | HCl | 133–138 |
| 13 | —CO—C$_6$H$_{13}$(n) | — | 195–197 |
| 14 | —CO—C$_6$H$_{13}$(n) | HCl | 135 |
| 15 | —CO—C$_{11}$H$_{23}$(n) | — | 175–177 |
| 16 | —CO—C$_{11}$H$_{23}$(n) | HCl | 163 |
| 17 | —CO—cyclopropyl | — | 246–250 |
| 18 | —CO—cyclopropyl | HCl | 232–234 |
| 19 | —CO—CH$_2$—Cl | | |
| 20 | —CO—C$_2$H$_4$—Cl | | |
| 21 | —CO—CH(Cl)—CH$_3$ | | |
| 22 | —CO—C$_3$H$_{6(n)}$—Cl | | |
| 23 | —CO—CH(Cl)—C$_2$H$_5$ | | |
| 24 | —CO—CH$_2$—OCH$_3$ | | |
| 25 | —CO—C$_2$H$_4$—OCH$_3$ | | |

TABLE 2

[Structure: (CH₃)₂CH-NH-C(=)- with triazine bearing H₂N and NHR₁]

| No. | R₁ | Salt | m.p. [°C.] |
|---|---|---|---|
| 1 | —CO—CH$_3$ | — | 202–204 |
| 2 | —CO—CH$_3$ | HCl | 80–90 (amorph) |
| 3 | —CO—C$_3$H$_7$(n) | — | 194–198 |
| 4 | —CO—C$_3$H$_7$(n) | HCl | 75–85 (amorph) |
| 5 | —CO—CH$_2$—Cl | | |
| 6 | —CO—C$_2$H$_4$—Cl | | |
| 7 | —CO—CH(Cl)—CH$_3$ | | |
| 8 | —CO—C$_3$H$_{6(n)}$—Cl | | |
| 9 | —CO—CH(Cl)—C$_2$H$_5$ | | |
| 10 | —CO—CH$_2$—OCH$_2$ | | |
| 11 | —CO—C$_2$H$_4$—OCH$_3$ | | |

TABLE 3

[Structure: cyclopropyl-C(=NH)-N=C(NHR')-N=C(NHR')- triazine-like system]

| No. | R' | Salt | m.p. [°C.] |
|---|---|---|---|
| 1 | —CO—C$_2$H$_5$ | — | 263–264 |
| 2 | —CO—CH$_3$ | — | 275 |
| 3 | —CO—C$_5$H$_{11}$ | — | 198–200 |
| 4 | —CO—cyclopropyl | — | 273–276 |
| 5 | —CO—cyclopropyl | HCl | 190 (decomp.) |
| 6 | —CO—C$_{11}$H$_{23}$ | — | 166–168 |
| 7 | —CO—(CH$_2$)$_3$—Cl | — | 193–194 |
| 8 | —CO—C$_4$H$_9$(t) | — | 65–70 (amorph) |
| 9 | —CO—C$_4$H$_9$(t) | HCl | 73–78 (amorph) |
| 10 | —CO—CH$_2$—Cl | | |
| 11 | —CO—C$_2$H$_4$—Cl | | |
| 12 | —CO—CH(Cl)—CH$_3$ | | |
| 13 | —CO—C$_3$H$_{6(n)}$—Cl | | |
| 14 | —CO—CH(Cl)—C$_2$H$_5$ | | |
| 15 | —CO—CH$_2$—OCH$_3$ | | |
| 16 | —CO—C$_2$H$_4$—OCH$_3$ | | |

TABLE 4

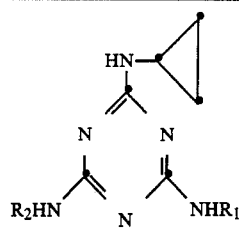

| No. | R$_1$ | R$_2$ | Salt | m.p. [°C.] |
|---|---|---|---|---|
| 1 | —CO—CH$_3$ | —CO—C$_2$H$_5$ | — | 259–262 |
| 2 | —CO—CH$_3$ | —CO—C$_2$H$_5$ | HCl | 155 (decomp.) |
| 3 | —CO—CH$_3$ | —CO—C$_3$H$_7$(n) | — | 232–233 |
| 4 | —CO—CH$_3$ | —CO—C$_3$H$_7$(n) | HCl | 215–217 (decomp.) |
| 5 | —CO—C$_2$H$_5$ | —CO—C$_3$H$_7$(n) | — | 242–244 |
| 6 | —CO—C$_2$H$_5$ | —CO—C$_3$H$_7$(n) | HCl | 217–219 (decomp.) |
| 7 | —CO—C$_3$H$_7$(n) | —CO—C$_6$H$_{13}$(n) | — | 180–182 |
| 8 | —CO—C$_3$H$_7$(n) | —CO—C$_6$H$_{13}$(n) | HCl | 120–124 |
| 9 | —CO—CH$_3$ | —CO—CH$_2$—Cl | | |
| 10 | —CO—CH$_3$ | —CO—CH$_2$H$_4$—Cl | | |
| 11 | —CO—CH$_3$ | —CO—CH(Cl)—CH$_3$ | | |
| 12 | —CO—C$_2$H$_5$ | —CO—C$_3$H$_{6(n)}$—Cl | | |
| 13 | —CO—C$_2$H$_5$ | —CO—CH(Cl)—C$_2$H$_5$ | | |
| 14 | —CO—CH$_3$ | —CO—CH$_2$—OCH$_3$ | | |
| 15 | —CO—CH$_3$ | —CO—C$_2$H$_4$—OCH$_3$ | | |

Example 7: Action againt *Lucilia sericata*

Freshly deposited eggs of the blowfly (L. sericata) are placed in small portions (30–50 eggs) into each test tube, in which there have previously been mixed 4 ml of nutrient medium with 1 ml of test solution in the intermediate dilution required for the final concentration. After the inoculation of the culture medium, the test tubes are closed with cotton-wool plugs, and are incubated in an incubator at 30° C. for 4 days. In the untreated medium serving as a comparison, larvae about 1 cm long (stage 3) have developed by the end of this period. When a substance is active, corresponding larvae up to this point of time are either dead, or moribund and clearly retarded. Tests are carried out simultaneously with concentrations of 10–0.01 ppm. The lowest fully effective concentration (LC 100) is taken as the criterion of effectiveness.

Embraced by the tests are both substances effective as contact poisons as well as substances effective as stomach poisons. Also taken into account is repellency, a factor resulting in the larvae migrating from the medium and starving to death.

Tested compounds Nos. 1–8, 10–12 and 14 from Table 1 and No. 1 from Table 2 are fully effective at concentrations of 0.1 to 0.5 ppm. Tested compounds 9, 13 and 16 from Table 1 and compound No. 9 from Table 3 have full effectiveness at concentrations of 1 to 2.5 ppm.

Example 8: Action against *Lucilia cuprina*

Freshly deposited eggs of the blowfly (L. cuprina) are placed in small portions (30–50 eggs) into each test tube in which there have previously been mixed 4 ml of nutrient medium with 1 ml of test solution in the intermediate dilution required for the final concentration. After the inoculation of the culture medium, the test tubes are closed with cotton-wool plugs, and are incubated in an incubator at 30° C. for 4 days. In the untreated medium serving as a comparison, larvae about 1 cm long (stage 3) have developed by the end of this period. When a substance is active, the corresponding larvae up to this point of time are either dead, or moribund and clearly retarded. Tests are carried out simultaneously with concentrations of 10–0.01 ppm. The lowest fully effective concentration (LC 100) is taken as the criterion of effectiveness.

Embraced by the tests are both substances effective as contact poisons as well as substances effective as stomach poisons. Also taken into account is repellency, a factor resulting in the larvae migrating from the medium and starving to death.

Tested compounds Nos. 1–8, 10–12 and 14 from Table 1 are fully effective at concentrations of 0.01 to 0.5 ppm. Tested compounds Nos. 9, 13 and 16 from Table 1 and compounds Nos. 1 and 9 from Table 3 have full effectiveness at concentrations of 1 to 2.5 ppm.

Example 9: Action against *Aedes aegypti*

Sufficient of a 0.1% acetonic solution of the respective active ingredient is transferred by pipette to the surface of 150 ml of water in a container to obtain concentrations in each case of 10, 5 and 1 ppm. After the acetone has been evaporated off, 30–40 three-day-old Aëdes larvae are placed into the container, and the mortality rate is ascertained after 1 2 and 5 days.

Compounds according to Examples 1–6 and Tables 1–4 effect a mortality rate of 100% at 1, 5 or 10 ppm.

Example 10: Action againt *Nilaparvata lugens* (nymphs) and *Laodelphax striatellus*

The test is carried out on growing rice plants. For this purpose, 4 plants (thickness of stem 8 mm: height about 20 cm) are planted in each of a number of pots (diameter 8 cm). The plants in each pot are sprayed on a rotary table with 100 ml of acetonic solutions containing 400 and 800 ppm, respectively, of active ingredient. After the sprayed-on coating has dried, each plant is infested with 20 nymphs of the test insects in the third stage. To prevent the cicadas from escaping, a glass cylinder is placed over each of the infested plants and is then closed with a gauze lid. The nymphs are kept for 10 days on the treated plant until the next development stage has been reached. An assessment of the mortality rate is made 1, 4 and 8 days after infestation.

Compounds from Examples 1-6 and Tables 1-4 exhibit a good level of effectiveness against nymphs of *Nilaparvata lugens* and of *Laodelphax striatellus*.

Example 11: Action against *Nilaparvata lugens* (ovicidal) and *Laodelphax striatellus*

The test is carried out on growing rice plants. For this purpose, 4 plants (thickness of stem 8 mm: height about 20 cm) are planted in each of a number of pots (diameter 8 cm). The plants in each pot are sprayed on a rotary table with 100 ml of an acetonic solution containing 400 ppm of active ingredient. After the sprayed-on coating has dried, 3 adult females are settled onto each plant. To prevent the insects from escaping, a glass cylinder is placed over each infested plant and is then closed with a gauze lid. The females remain for 4 days on the treated plant for oviposition, and are subsequently removed.

About 8 days after infestation, the young cicadas hatch and an assessment is made. The mortality rate is determined by the comparison of the number of hatched larvae on the treated plants with the number of hatched larvae on the untreated control plants.

Compounds from Examples 1-6 and Tables 1-4 exhibit in the above test an ovicidal action exceeding 80%.

Active ingredient preparations

The active ingredients of the formula I can be formulated for example as follows:

Granulate 5 parts of active ingredient,
0.25 part of epoxidised vegetable oil,
0.25 part of cetyl polyglycol ether,
3.50 parts of polyethylene glycol, and
91 parts of kaolin (particle size 0.3-0.8 mm).

The active ingredient is mixed with the epoxidised vegetable oil; the mixture is dissolved in 6 parts of acetone, and the polyethylene glycol and cetyl polyglycol ether are then added. The resulting solution is sprayed onto kaolin, and the acetone is subsequently evaporated off in vacuo. Granulates of this type can be added to the animal feed.

Dust 5 parts by weight of finely ground active ingredient are thoroughly mixed with
2 parts by weight of a precipitated silicic acid and
93 parts by weight of talcum.

The active ingredient is homogeneously mixed and ground with the carriers. The dust can be used not only externally but also as an additive to the animal feed.

Wettable powder 5 to 30 parts by weight of active ingredient are vigorously mixed, in a mixing apparatus, with
5 parts by weight of an absorbent carrier (silicic acid K 320 or Wessalon S) and
55 to 80 parts by weight of a carrier [bolus alba or kaolin (B 24)] and a dispersing agent mixture consisting of 5 parts by weight of sodium lauryl sulfonate and 5 parts by weight of alkyl-aryl-polyglycol ether.

This mixture is ground in a dowelled disk mill or air jet mill to a particle size of 5-15 μm. The wettable powder thus obtained gives a good suspension in water.

Emulsion concentrate 20 parts by weight of active ingredient are dissolved in
70 parts by weight of xylene, and to the solution are added
10 parts by weight of an emulsifier consisting of a mixture of an alkylphenylpolyglycol ether and the calcium salt of dodecylbenzenesulfonic acid.

A milky emulsion can be prepared by adding water in any desired proportion to the above emulsion concentrate, and this emulsion can be added to the drinking water for the animals.

Pour-on solution

| active ingredient | 30.00 g |
|---|---|
| sodium dioctylsulfosuccinate | 3.00 g |
| benzyl alcohol | 35.46 g |
| ethylene glycol monomethyl ether | 35.46 g |
| | 103.92 g = 100 ml. |

The active ingredient is dissolved in the major part of the mixture of the two solvents with vigorous stirring. The sodium dioctylsulfosuccinate is subsequently dissolved therein, if necessary with heating, and finally the remaining part of the solvent mixture is added.

What is claimed is:

1. A compound of the formula I

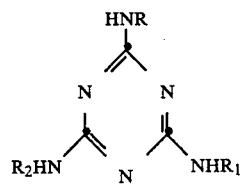

wherein
R is cyclopropyl,
R$_1$ is hydrogen, and
R$_2$ is C$_2$-C$_{12}$-acyl.

2. 2-Cyclopropylamino-4-acetylamino-6-amino-1,3,5-triazine according to claim 1.

3. 2-Cyclopropylamino-4-propanoylamino-6-amino-1,3,5-triazine according to claim 1.

4. 2-Cyclopropylamino-4-butanoylamino-6-amino-1,3,5-triazine according to claim 1.

5. 2-Cyclopropylamino-4-(2-methylpropanoylamino)-6-amino-1,3,5-triazine according to claim 1.

6. An insecticidal or larvacidal composition which comprises as active ingredient a compound according to claim 1, together with a carrier further additive.

7. A method for controlling ectoparasites of productive animals, which process comprises applying to the exterior of said animals an ectoparasiticidally effective amount of a compound of formula I of claim 1.

8. A method according to claim 7 for controlling ectoparasites which are members of the order Diptera.

9. A method for controlling insects inhabiting the faeces of useful animals, which method comprises peroral administration to the useful animals of an insecticidally effective amount of a compound of formula I of claim 1.

10. A method according to claim 9 for controlling insects which are members of the order Diptera.

* * * * *